United States Patent [19]

Kishimoto et al.

[11] 4,096,263
[45] Jun. 20, 1978

[54] 1,2,3,4-TETRAHYDROISOQUINOLINES AND THE PREPARATION THEREOF

[75] Inventors: Teiji Kishimoto, Kawanishi; Ikuo Ueda, Yao; Masayuki Kato, Ikeda, all of Japan

[73] Assignee: Fujisawa Pharmaceutical Co., Ltd., Osaka, Japan

[21] Appl. No.: 707,271

[22] Filed: Jul. 21, 1976

[30] Foreign Application Priority Data

Jul. 28, 1975 United Kingdom ............... 31570/75

[51] Int. Cl.² ................... A61K 31/47; A61K 31/505; C07D 239/42
[52] U.S. Cl. ............................. 424/251; 260/288 CE; 424/258; 544/331; 544/238; 544/405; 544/405; 544/332; 544/336; 544/224
[58] Field of Search ................... 260/288 CE, 256.4 B, 260/283 SY, 256.4 N; 424/258, 251

[56] References Cited

U.S. PATENT DOCUMENTS

| | | | |
|---|---|---|---|
| 3,389,140 | 6/1968 | Montzka | 260/286 |
| 3,963,725 | 6/1976 | Kishimoto et al. | 260/288 CE |
| 3,978,063 | 8/1976 | Kishimoto et al. | 260/288 CE |
| 3,994,891 | 11/1976 | Hughes et al. | 260/288 CE |

*Primary Examiner*—Paul M. Coughlan, Jr.
*Attorney, Agent, or Firm*—Oblon, Fisher, Spivak, McClelland & Maier

[57] ABSTRACT

1,2,3,4-Tetrahydroisoquinolines of the formula

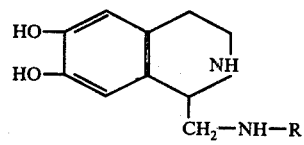

wherein R is a heterocyclic group which may have appropriate substituent(s) and pharmaceutically acceptable salts thereof, which have relaxing activity on smooth muscle, are disclosed, together with a method for their preparation.

20 Claims, No Drawings

1,2,3,4-TETRAHYDROISOQUINOLINES AND THE PREPARATION THEREOF

The present invention relates to 1,2,3,4-tetrahydroisoquinolines and pharmaceutically acceptable salts thereof, which have a relaxing affect on smooth muscles, and to a process for the preparation thereof.

The 1,2,3,4-tetrahydroisoquinolines of the present invention are represented by the formula:

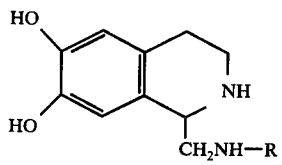
(I)

wherein R is a heterocyclic group which may be substituted with an appropriate substituent(s).

In this specification, the term "lower" is intented to mean 1 to 6 carbon atom(s) unless otherwise specified.

The heterocyclic groups include saturated or unsaturated, mono- or condensed heterocyclic groups which have at least one hetero atom selected from the group consisting of nitrogen, sulfur, oxygen and the like.

Suitable heterocyclic groups include an unsaturated 3 to 8 membered heteromonocyclic group having 1 to 4 nitrogen atom(s), for example, pyrrolyl, pyrrolinyl, imidazolyl, pyrazolyl, pyridyl, pyrimidinyl, pyrazinyl, pyridazinyl, triazolyl (e.g. 4H-1,2,4-triazolyl, 1H-1,2,3-triazolyl, etc.), tetrazolyl (e.g., 1H-tetrazolyl, 2H-tetrazolyl, etc.), etc.; a saturated 3 to 8 membered heteromonocyclic group having 1 to 2 nitrogen atom(s) (e.g., pyrrolidinyl, imidazolidinyl, piperidyl, piperazinyl, etc.); an unsaturated condensed-heterocyclic group having 1 to 4 nitrogen atom(s) such as the heterocyclic group fused to benzene (e.g., indolyl, isoindolyl, indazolyl, quinolyl, isoquinolyl, benzotriazolyl, benzimidazolyl, etc.) or the heterocyclic group fused to heterocyclic group (e.g., purinyl, etc.);

an unsaturated 3 to 8 membered heteromonocyclic group having a sulfur atom (e.g., thienyl, etc.);

an unsaturated condensed-heterocyclic group having a sulfur atom (e.g., benzothienyl, etc.);

an unsaturated 3 to 8 membered heteromonocyclic group having an oxygen atom (e.g., furyl, pyranyl, etc.);

a saturated 3 to 8 membered heteromonocyclic group having an oxygen atom (e.g., tetrahydrofuryl, tetrahydropyranyl, etc.);

an unsaturated condensed-heterocyclic group having an oxygen atom (e.g., benzofuranyl, chromenyl, xanthenyl, etc.);

an unsaturated 3 to 8 membered heteromonocyclic group having an oxygen atom and 1 to 3 nitrogen atom(s) (e.g., oxazolyl, isoxazolyl, oxadiazolyl, etc.);

an unsaturated condensed-heterocyclic group having an oxygen atom and 1 to 2 nitrogen atom(s) (e.g., benzoxazolyl, benzoxadiazolyl, etc.);

an unsaturated 3 to 8 membered heteromonocyclic group having a sulfur atom and 1 to 3 nitrogen atom(s), for example, thiazolyl, isothiazolyl, thiadiazolyl (e.g., 1,2,4-thiadiazolyl, 1,3,4-thiadiazolyl, 1,2,5-thiadiazolyl, etc.) etc.;

an unsaturated condensed-heterocyclic group having a sulfur atom and 1 to 2 nitrogen atom(s) (e.g., benzothiazolyl, benzothiadiazolyl, etc.), and the like, and said heterocyclic groups may have optionally one or more appropriate substituent(s) selected from the group consisting of lower alkyl having 1 to 6 carbon atom(s) (e.g., methyl, ethyl, propyl, isopropyl, butyl, isobutyl, tert-butyl, pentyl, hexyl, etc.), cyclo(lower)alkyl having 1 to 6 carbon atom(s) (e.g., cyclopropyl, cyclobutyl, cyclopentyl, cyclohexyl, etc.), lower alkenyl having 2 to 6 carbon atoms (e.g., vinyl, 1-propenyl, allyl, isopropenyl, 2-butenyl, etc.), aryl having 6 to 10 carbon atoms (e.g., phenyl, tolyl, xylyl, mesityl, cumenyl, etc.), oxo, nitro and the like, in which the aryl group may further have one or more appropriate substituent(s) selected from the group consisting of halogen (e.g., chlorine, bromine, fluorine or iodine), lower alkoxy having 1 to 6 carbon atoms(s) (e.g., methoxy, ethoxy, propoxy, isopropoxy, butoxy, isobutoxy, tert-butoxy, etc.) and the like.

Suitable pharmaceutically acceptable salts of compound (I) include acid addition salts of inorganic acids (e.g., hydrochloric acid, hydrobromic acid, hydriodic acid, sulfuric acid, etc.) or an organic acid (e.g., acetic acid, malic acid, tartaric acid, maleic acid, fumaric acid, etc.), and a quaternary salt with a lower alkyl halide (e.g., methyl iodide, ethyl bromide, etc.) or the like.

The 1,2,3,4-tetrahydroisoquinolines (I) of the invention can be prepared by reacting a 3,4-dihydroxyphenethylamine of the formula:

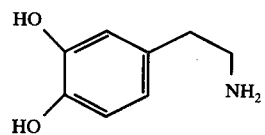
(II)

or a salt thereof with a compound of the formula:

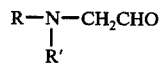
(III)

wherein R is as defined above and R' is hydrogen or a protective group for amino, or the reactive equivalent thereof, or the salt thereof.

Suitable salt of the compound (II) may include an inorganic acid salt (e.g., hydrochloride, sulfate, hydrobromide, hydriodide, carbonate, etc.) and an organic acid salt (e.g., acetate, fumarate, maleate, tartarate, etc.).

Suitable protective groups for amino include acyl which is conventionally used as protective group for amino such as lower alkanoyl (e.g., formyl, acetyl, propionyl, etc.); mono (or di or tri) halo(lower)alkanoyl (e.g., chloroacetyl, trifluoroacetyl, etc.);

ar(lower)alkanoyl, for example, phenyl(lower)alkanoyl (e.g., phenylacetyl, phenylpropionyl, etc.) or the like;

ar(lower)alkoxycarbonyl which may have suitable substituent(s), for example, phenyl(lower)alkoxycarbonyl (e.g., benzyloxycarbonyl, phenethyloxycarbonyl, phenylpropyloxycarbonyl, etc.), halophenyl(lower)alkoxycarbonyl (e.g., 2-bromobenzyloxycarbonyl, 4-chlorobenzyloxycarbonyl, 4-bromobenzyloxycarbonyl, etc.), nitrophenyl(lower)alkoxycarbonyl (e.g., 4-nitrobenzyloxycarbonyl, etc.), mono(or di)-(lower)alkoxyphenyl(lower)alkoxycarbonyl (e.g., 4-methoxybenzyloxycarbonyl, 3,4-dimethoxybenzyloxycarbonyl, etc.), phenylazophenyl(lower)alkoxycarbonyl (e.g., 4-(phenylazo)benzyloxycarbonyl, etc.), or the like;

lower alkxoycarbonyl (e.g., methoxycarbonyl, ethoxycarbonyl, isopropoxycarbonyl, 1-cyclopropylethoxycarbonyl, tert-butoxycarbonyl, 1,1-dimethylpropoxycarbonyl, etc.; mono (or di or tri) halo(lower)alkoxycarbonyl (e.g., trichloroethoxycarbonyl, tribromoethoxycarbonyl, etc.);

aroyl having 7 or 8 carbon atoms (e.g., benzoyl, toluoyl, etc.);

lower alkanesulfonyl (e.g., mesyl, ethanesulfonyl, propanesulfonyl, etc.);

arenesulfonyl having 6 or 7 carbon atoms (e.g., benzenesulfonyl, tosyl, etc.);

heterocyclic oxycarbonyl (e.g., 8-quinolyloxycarbonyl, etc.); 2-pyridylmethoxycarbonyl; adamantyloxycarbonyl; or the like, and other conventional protective groups for amino.

Suitable salts of the compound (III) include quaternary salt with lower alkyl halide (e.g., methyl iodide, ethyl bromide, etc.) and the like.

The reactive equivalent of the compound (III) include all compounds having equivalent workability to the compound (III) in this reaction. Suitable example of such reactive equivalent include (a) a derivative on the formyl group of the compound (III) such as acetal, hemiacetal, hydrate(diol), mono or diacylated diol, thioacetal, hemithioacetal, Schiff's base or its tautomeric enamines, oxime, semicarbazone, thiosemicarbazone, alkoxalyl (e.g., methoxalyl, ethoxyalyl, etc.) and the like; (b) a compound wherein the formylmethylene group of the aldehyde compound (III) is in a form of 2-acyloxyvinyl (e.g., 2-acetoxyvinyl, 2-propionyloxyvinyl, etc.), 2-lower alkoxyvinyl (e.g., 2-methoxyvinyl, 2-ethoxyvinyl, 2-propoxyvinyl, 2-isopropoxyvinyl, etc.), 2-lower alkylthiovinyl (e.g., 2-methylthiovinyl, 2-ethylthiovinyl, 2-propylthiovinyl, etc.), 2-aminovinyl, and (c) a compound substituted with the symbol Z (wherein Z is carboxy or its derivative) for one hydrogen atom on the methylene group adjacent to the formyl group of the compounds (III) or reactive equivalent thereof as mentioned in the above (a) or (b).

Suitable example of the derivative of the carboxy group for Z may be an ester such as a saturated or unsaturated, cyclic or acyclic aliphatic hydrocarbon ester (e.g., methyl ester, ethyl ester, propyl ester, isopropyl ester, butyl ester, t-butyl ester, cyclohexyl ester, cycloheptyl ester, vinyl ester, 1-propenyl ester, 2-propenyl ester, 3-butenyl ester, etc.), an aryl ester (e.g., phenyl ester, xylyl ester, tolyl ester, naphthyl ester, etc.), an aralkyl ester (e.g., benzyl ester, phenethyl ester, etc.) and the like; an amide such as a N-lower alkyl amide (e.g., N-methyl amide, N-ethyl amide, etc.), a N-aryl amide (e.g., N-phenyl amide, etc.) a N,N-di(lower alkyl) amide (e.g., N,N-dimethylamide, N,N-diethyl amide, N-ethyl-N-methyl amide, etc.), and other amide with imidazole, 4-substituted imidazole, etc. and the like; and anhydrides such as a mixed anhydride with a dialkylphosphoric acid, dibenzylphosphoric acid, a halogenated phosphoric acid, a dialkylphosphorous acid, sulfurous acid, thiosulfuric acid, sulfuric acid, an alkylcarbonic acid, an aliphatic carboxylic acid (e.g., pivalic acid, pentanoic acid, isopentanoic acid, 2-ethylbutanoic acid, chloroacetic acid, etc.), or an aromatic carboxylic acid (e.g., benzoic acid, etc.); or a symmetrical anhydride.

The present reaction is preferably conducted in the presence of an acid. Suitable acid includes, for example, an inorganic acid (e.g., hydrochloric acid, hydrobromic acid, sulfuric acid, phosphoric acid, etc.) and an organic acid (e.g., acetic acid, chloroacetic acid, trifluoroacetic acid, propionic acid, methanesulfonic acid, etc.). The reaction can be conducted with or without solvent. Suitable solvent includes, for example, methanol, ethanol, n-butanol, water, benzene, chloroform, dioxane, a buffer solution and the like, and the mixture thereof. There is no particular limitation to the present reaction temperature, and the present reaction can be conducted from cold temperatures to elevated temperature and more usually at ambient temperature, warming or heating around the boiling point of the solvent.

The starting compound (III) and reactive equivalent thereof are novel compounds and can be prepared by a) reacting a compound of the formula:

(IV)

wherein R and R' are each as defined above, with a compound of the formula:

$$X-CH_2CHO \qquad (V)$$

wherein X is an acid residue, or derivative thereof, or b) reacting a compound of the formula:

$$R-X \qquad (VI)$$

wherein R and X are each as defined above, with a compound of the formula:

(VII)

wherein R' is as defined above, or derivative thereof. If the resultant compound produced by either of the abovementioned reactions a) or b) is a compound of the formula:

$$R-NH-CH_2CHO \qquad (III')$$

wherein R is as defined above, or a derivative therof, then, if necessary, the compund (III') or derivative thereof can be reacted with an appropriate compound to protect the amino group.

Suitable acid residues include halogen such as bromine, chlorine, iodine and fluorine.

Suitable derivatives of the compound (V), (VII) and (III') are included among those compounds which are reactive equivalents to compounds (III).

The reactions of the compound (IV) with the compound (V) or derivtive thereof and of the compound (VI) with the compound (VII) or derivative thereof are usually conducted in a solvent such as dimethylformamide, hexamethylphosphoric triamide, benzene, toluene, dimethylsulfoxide, an alcohol (e.g., methanol, etc.) or any other organic solvent which does not adversely affect the reaction. These solvents may be used as mixture thereof.

The present reactions are preferably conducted in the presence of a base, for example, an inorganic base such as an alkali metal hydride (e.g., sodium hydride, potassium hydride, etc.), an alkali metal hydroxide (e.g., sodium hydroxide, potassium hydroxide, etc.), an alkali metal bicarbonate (e.g., sodium bicarbonate, potassium bicarbonate, etc.) or alkali metal carbonate (e.g., sodium carbonate, potassium carbonate, etc.), an organic base such as an alkali metal alkoxide (e.g., sodium methoxide, sodium ethoxide, etc.), a trialkylamine (e.g., trimethylamine, triethylamine, etc.), triethanolamine, N,N-dimethylaniline, N,N-dimethylbenzylamine, N-methylmorpholine or pyridine.

The reaction temperatures are not critical and the reactions are usually conducted with cooling, at ambient temperature, under warming and heating.

In case that the resultant compound obtained by the above-mentioned reactions is the compound (III') or derivative thereof, said resultant compound (III') or derivative thereof is, if necessary, subjected to an introduction reaction of a protective group for amino.

The present introduction reaction is carried out by reacting the compound (III') or derivative thereof with a compound of the formula:

R'' — OH (VIII)

wherein R'' is acyl or reactive derivative thereof, when the protective group for amino to be introduced is acyl group.

Suitable acyl for R'' can be referred to the one as exemplified for the protective group for amino.

Suitable reactive derivatives of the compound (VIII) include, for example, an acid halide, an acid anhydride, an activated amide, an activated ester, and preferably an acid chloride; an acid azide;

a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid, trichloroacetic acid, etc.), aromatic carboxylic acid (e.g., benozic acid, etc.), or a symmetrical acid anhydride;

an acid amide with imidazole, 4-substituted imidazole, dimethylpyrazole, triazole or tetrazole; or an ester (e.g., cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), or the like. The suitable reactive derivative can be optionally selected from them according to the kind of the compound (VIII) to be used practically.

The reaction of the compound (III') with the compound (VIII) is usually conducted in a solvent such as water, acetone, dioxane, acetonitrile, chloroform, methylene chloride, ethylene chloride, tetrahydrofuran, ethyl acetate, dimethylformamide, hexamethylphosphoric triamide, pyridine or any other organic solvent which does not adversely affect the reaction. These solvents may be used as a mixture thereof.

When the compound (VIII) is used in a form of the free acid or salt in this reaction, the reaction is preferably conducted in the presence of a condensing agent such as N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)-carbodiimide, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethyl-benzisoxazolium salt, N-ethyl-5-phenyl-isoxazolium-3'-sulfonate, Vilsmeier reagent such as (chloromethylene)dimethylammonium chloride or the like, or the like.

Also, the reaction may be conducted in the prsence of a base, for example, an inorganic base such as an alkali metal hydride, an alkali metal hydroxide, an alkali metal bicarbonate or an alkali metal carbonate; or an organic base such as trialkylamine, N,N-dialkylbenzylamine, an alkali metal alkoxide, N,N-dialkylaniline or pyridine. When the base or the condensing agent is in liquid, it can also be used as a solvent. The reaction temperature is not critical, and the reaction is usually conducted under cooling, at ambient temperature, under warming or heating.

Thus obtained compound (III) or reactive equivalent thereof may be, if necessary, converted into quaternary salt thereof as mentioned above by conventional methods.

The object compound (I) of the present invention obtained above may be, if necessary, converted into pharmaceutically acceptable salts thereof by conventional methods.

The new 1,2,3,4-tetrahydroisoquinolines (I) of the present invention and the pharmaceutically acceptable salts thereof have relaxing activity on smooth muscles, especially on vacuslar -and visceral-smooth muscles. Accordingly, they show vasodilating, intestinal-contraction inhibiting and bladder-contraction inhibiting effects together with some bronchodilating effects, and are useful as vasodilator, intestinal-contraction inhibitor and bladder-contraction inhibitor. Thus, the compound (I) of the present invention and the pharmaceutically acceptable salts thereof are useful medicinals in the treatment of spasmodic disorders of visceral organs, e.g., colonic irritability, chronic cholecystitics, etc. in mammals.

The 1,2,3,4-tetrahydroisoquinolines (I) and the pharmaceutically acceptable salts thereof of the present invention can be administered by the conventional methods, the conventional types of unit dosages or with the conventional pharmaceutical carriers to roduce relaxing activities on smooth muscles.

Thus, they can be used in the form of pharmaceutical preparations, which contain them in admixture with a pharmaceutical organic or inorganic carrier material suitable for enteral or parenteral applications. Oral administration by the use of tablets capsules or in liquid form such as suspensions, solutions or emulsions is particularly advantageous. When formed into tablets, the conventional binding and disintegrating agents used in therapeutic unit dosages can be employed. Suitable binding agents include glucose, lactose, gum acacia, gelatin, mannitol, starch paste, magnesium trisilicate and talc. Suitable disintegrating agents include corn starch, keratin, colloidal silica and potato starch. When administered as liquids the conventional liquid carriers can be used.

The unit dosage or therapeutically effective quantity of the compounds (I) and the pharmaceutically acceptable salts thereof for human beings can vary over wide limits such as that of 0.01 milligram to about 100 milligrams. The upper limit is limited only by the degree of effect desired and economical considerations. For oral administration it is preferable to employ from about 1 milligram to about 100 milligrams of the therapeutic agent per unit dosage. It is indicated from animal experiments that about 0.1 to about 10 milligrams dosages amdinistered orally three times daily as needed will provide a preferred daily dosage. Of course, the dosage of the particular therapeutic agent used can vary considerably depending on such factors as the age of the patient and the degree of therapeutic effect desired. Each unit dosage form of the novel therapeutic compounds can contain from about 0.5 to about 99.5% of the novel therapeutic agents by weight of the entire composition with the remainder comprising conventional pharmaceutical carriers. By the term pharmaceutical carrier it is intended to include non-therapeutic materials which are conventionally used with unit dosage and include fillers, diluents, binders, lubricants, disintegrating agents and solvents. Of course, it is possible to administer the novel therapeutics, i.e. the pure compounds, without the use of a pharmaceutical carrier. It is also possible to administer the new 1,2,3,4-tetrahydroisoquinolines (I) and the pharmaceutically acceptable salts thereof in the form of mixture with other agents which are used as a relaxant on smooth muscles and especially on vascular-smooth and visceral-smooth muscles.

Now relaxing activity on smooth muscles of the typical compound which falls within the category of the compounds of the formula (I) of this invention is illustrated in reference to a test in which active ingredient is the following compound.

Test Compound 1-(1-Methyl-1H-tetrazol-5-yl)aminomethyl-6,7-dihydroxy-1,2,3,4-tetrahydroisoquinoline hydrochloride trihemihydrate

TEST

Intestinal Motility in Dogs

Method: Mongrel dogs weighing 8 to 16 kg which were withheld from any food and water for 24 hours were anesthetized with a combination of urethane (1.5 g/kg) and morphine (15 mg/kg). A balloon was placed at the jejunum of the dog, compressed at a pressure of 10 cm. $H_2O$, and connected to a strain gauge. Changes in the motility were mainly recorded in terms of amplitude, but taking account of the number of movements. The maximum change of all the determinations, served as the calculation of the 50% inhibition dose ($ED_{50}$). The time required for 80% recovery was considered as a duration of action. Results are shown in the following table.

| $ED_{50}$(μg/kg) | Duration of Action (min.) |
| --- | --- |
| 1 | 25 |

Practical and presently-preferred embodiments of this invention are shown in the following Examples.

EXAMPLE 1

(a) Preparation of the starting compound (1) 1-Methyl-5-amino-1H-tetrazole (26 g.) was added to a suspension of 50% sodium hydride (25.5g.) in a mixture of dried dimethylformamide (50 ml.) and dried hexamethylphosphoric triamide (50 g.) with stirring and cooling with dry icemethanol bath. The reaction temperature was elevated and after 20 minutes, the mixture was stirred for 15 minutes under ice-cooling, and then stirred at ambient temperature. To the resultant mixture was added dried dimethylformamide (70 ml.) and then gradually added bromoacetaldehyde diethyl acetal (53 g.) at ambient temperature, and the mixture was stirred for 4 hours at ambient temperature and for 1 hour at 50° C. The reaction mixture was cooled with ice and ice-water was added thereto. The mixture was extracted 3 times with ethyl acetate. The extract was in turn washed twice with water and a saturated sodium chloride aqueous solution, and dried over magnesium sulfate. The solution was concentrated under reduced pressure and the residual oil was subjected twice to azeotropic distillation with toluene. To the residue were added benzene and n-hexane and the mixture was allowed to stand at 5° C to precipitate crystals. The crystals were collected by filtration to give (1-methyl-1H-tetrazol-5-yl)-aminoacetaldehyde diethyl acetal (11 g.). The mother liquor was concentrated and the residue was purified by column chromatography on silica gel using a mixture of benzene: chloroform (1 : 1) as developing solvent. The obtained oil was crystallized by a mixture of benzene and n-hexane to give the object compound (9.35 g.). Total yield (20.35 g.), mp 99° to 101° C.

Infrared Absorption Spectrum (Nujol) 1620 $cm^{-1}$.

Nuclear Magnetic Resonance Spectrum ($CDCl_3$, δ) ppm 6.90 (1H, broad t, J=6Hz); 4.70 (1H, t, J=5.4Hz); 3.80 (3H, s); 3.50 (6H, m); 1.09 (6H, t, J=7Hz).

(2) A mixture of dried dimethylsulfoxide (15 l), potassium hydroxide powder (2.58 kg) and 1-methyl-5-amino-1H-tetrazole (1.14 kg) was vigorously stirred for 1 hour at ambient temperature. Bromoacetaldehyde diethyl acetal (4.53 kg) was dropwise added thereto over 20 minutes. The mixture was stirred for 4 hours at ambient temperature and poured into a solution of sodium chloride (10 kg) in water (20 l) and ice (10 kg). The resulting mixture was stirred for 2 hours and allowed to stand under ice-cooling. Precipitating crystals were collected by filtration and dissolved in a mixture of ethyl acetate and acetone (1 : 1) (40 l). An insoluble material was filtrerd off and the filtrate was concentrated under reduced pressure to give yellowish white crystals. The crystals were washed with n-hexane (10 l) and dried to give (1-methyl-1H-tetrazol-5-yl)-aminoacetaldehyde diethyl acetal (1.77 kg). This compound was identified with the compound obtained in Example 1 (a) (1) by mp, I.R. and N.M.R. spectra.

(b) Preparation of the object compound (1) (1-methyl-1H-tetrazol-5-yl)aminoacetaldehyde diethyl acetal (21.5 g.) and 3,4-dihydroxyphenethylamine hydrochloride (14.6 g.) were added to a mixture of ethanol (130 ml.) and water (35 ml.), and dissolved with heating and stirring. Conc. hydrochloric acid (10.5 ml.) was added thereto and the mixture was refluxed for 8 hours. The reaction mixture was treated with activated charcoal. The charcoal was filtered and washed with ethanol, after which the filtrate and the washings were combined and concentrated under reduced pressure. The residual crystals were recrystallized from a mixture of water and isopropyl alcohol and the obtained crystals (22.5 g.) were warmed for 16 hours at 60° C under reduced pressure to remove excess hydrogen chloride. The crystals were recrystallized from a mixture of a small amount of water, methanol and ether to give 1-(1-methyl-1H-tetrazol-5-yl)aminomethyl-6,7-dihydroxy-1,2,3,4-tetrahydroisoquinoline hydrochloride trihemihydrate (15 g.), mp 107° to 110° C. Infrared Absorption Spectrum (Nujol) 1604, 1460 cm$^{-1}$.

Nuclear Magnetic Resonance Spectrum (d$_6$-DMSO, δ) ppm 9.70 (1 H, broad s); 9.30 (1H, broad s); 7.60 (1H, m); 6.77 (1H, s); 6.63 (1H, s); 4.60 (1H, m); 3.90 (3H, s); 3.76 (2H, m); 3.33 (2H, m); 2.90 (2H, m).

Analysis Calcd. for $C_{12}H_{16}O_2N_6 \cdot HCl \cdot 3/2H_2O$: C 46.08, H 5.48, N 26.87, Cl 11.34.
Found: C 45.84, H 5.40, N 26.85, Cl 11.75.

(2) A solution of 3,4-dihydroxyphenethylamine hydrochloride (1.76 kg), (1-methyl-1H-tetrazol-5-yl)-aminoacetaldehyde diethyl acetal (2.01 kg) and conc. hydrochloric acid (40 ml) in water (2 l) was stirred for 1 hour at 85° C. The reaction mixture was poured into acetone (20 l), to which was added conc. hydrochloric acid (1.5 l). After stirring for 1 hour, the mixture was allowed to stand under ice-cooling. Precipitating crystals were collected by filtration, washed with acetone and dried to give crystals (3.00 kg). The crystals were dissolved in water (4 l) and an insoluble material was filtered off. The filtrate was poured into acetone (20 l) at 50° C, to which was added conc. hydrochloric acid (1.5 l). After stirring, the resultant mixture was allowed to stand under ice-cooling. Precipitating crystals were collected by filtration, washed with acetone and dried to give crystals (2.22 kg). The crystals were dissolved in water (6.0 l) at 80° C and conc. hydrochloric acid (1.5 l) was added thereto. The mixture was allowed to stand under ice-cooling and precipitating crystals were collected by filtration, washed with water and dried under reduced pressure to give 1-(1-methyl-1H-tetrazol-5-yl)aminomethyl-6,7-dihydroxy-1,2,3,4-tertrahydroisoquinoline dihydrochloride (1.89 kg), mp 105° to 106° C and 213° to 215° C (dec.).

I.R. spectrum (Nujol). 1677, 1572, 1458 cm$^{-1}$.

N.M.R. spectrum (d$_6$-DMSO, δ) ppm 9.16 ~ 10.16 (5H, m); 7.83 (1H, broad s); 6.77 (1H, s); 6.61 (1H, s); 4.78 (2H, m); 4.53 (1H, m); 3.87 (3H, s); 3.33 (2H, m); 2.88 (2H, m). Analysis Calcd. for $C_{12}H_{18}O_2N_6Cl_2$: C, 41.27; H, 5.19; N, 24.07; Cl 20.30. Found: C, 41.15; H, 5.13; N, 24.41, Cl 19.72.

A mixture of 1-(1-methyl-1H-tetrazol-5-yl)aminomethyl-6,7-dihydroxy-1,2,3,4-tetrahydroisoquinoline dihydrochloride (52.3 g) and water (300 ml) was stirred for 15 minutes at 100° C to give homogeneous solution. Fumaric acid (11.3 g) was added thereto at 100° C, to which was added water (50 ml). The mixture was stirred for 15 minutes, to which were added sodium bicarbonate (25.2 g) over 12 minutes and water (50 ml). The resultant mixture was stirred for 20 minutes at 100° C and the reaction mixture was filtered. The filtrate was allowed to stand at ambient temperature to precipitate crystals. The crystals were collected by filtration, washed with water and dried under reduced pressure to give 1-(1-methyl-1H-tetrazol-5-yl)aminomethyl-6,7-dihydroxy-1,2,3,4-tetrahydroisoquinoline hemifumarate (42.05 g), mp 204° to 207° C (dec.).

I.R. spectrum (Nujol) 1620, 1564, 1534, 1460 cm$^{-1}$.
N.M.R. spectrum (d$_6$-DMSO, δ); ppm 9.00 (5H, m); 7.60 (1H, s); 7.53 (1H, s); 7.45 (1H, s); 5.33 (1H, m); 4.75 (2H, m); 4.17 (2H, m); 3.75 (2H, m). Analysis Calcd. for $C_{14}H_{18}O_4N_6$: C, 50.36; H, 5.43; N, 25.14. Found: C, 49.99; H, 5.46, N, 24.98.

EXAMPLE 2

(a) Preparation of the starting compound

A solution of 1-phenyl-5-amino-1H-tetrazole (10 g.) in dried dimethylformamide (50 ml.) was dropwise added to a suspension of 50% sodium hydride (5.1g.) in dried dimethylformamide (5 ml.) over 15 minutes under ice-cooling, and the mixture was stirred for 30 minutes at ambient temperature. To the resultant mixture was added a solution of bromoacetaldehyde diethyl acetal (13.5 g.) in dried dimethylformamide (15 ml.). The mixture was stirred for 1 hour at ambient temperature and for 2 hours and 20 minutes at 60° C. The reaction mixture was cooled to at ambient temperature, ice-water was added thereto and the mixture was extracted 3 times with ethyl acetate. The extract was washed with water and a saturated sodium chloride aqueous solution, and dried over magnesium sulfate. The solvent was distilled off under reduced pressure and the obtained oil was purified by column chromatography on silica gel (250 g.) using chloroform as developing solvent to give (1-phenyl-1H-tetrazol-5-yl)aminoacetaldehyde diethyl acetal (11 g.), oil.

Infrared Absorption Spectrum (Nujol) 1607, 1140, 1070 cm$^{-1}$.

Nuclear Magnetic Resonance Spectrum (d$_6$-DMSO, δ) ppm 7.61 (5H, s); 7.0 (1H, t, J=6.5Hz); 4.77 (1H, t, J=6Hz); 3.50 (6H, m); 1.10 (6H, t, J=7Hz).

(b) Preparation of the object compound (1-phenyl-1H-tetrazol-5-yl)aminoacetaldehyde diethyl acetal (11 g.) and 3,4-dihydroxyphenethylamine hydrochloride (5.0 g.) were added to a mixture of ethanol (55 ml.) and water (20 ml.), and dissolved with heating and stirring. Conc. hydrochloric acid (6.0 g.) was added thereto and the mixture was refluxed for 8 hours. The reaction mixture was allowed to stand and the precipitated crystals were collected by filtration to give 1-(1-phenyl-1H-tetrazol-5-yl)aminomethyl-6,7-dihydroxy-1,2,3,4-tetrahydroisoquinoline hydrochloride (5.9 g.). The crystals were recrystallized from a mixture of isopropyl alcohol and water to give pure crystals (4.2 g.), mp 236° to 241° C (dec.).

Infrared Absorption Spectrum (Nujol) 1623, 1598, 1457 cm$^{-1}$.

Nuclear Magnetic Resonance Spectrum (d$_6$-DMSO, δ) ppm 9.40 (4H, m); 7.75 (5H, m); 6.75 (1H, s); 6.62 (1H, s); 4.60 (1H, m); 3.75 (2H, m); 3.30 (2H, m); 2.86 (2H, m). Analysis Calcd. for $C_{17}H_{19}O_2N_6Cl$: C, 54.48; H, 5.11; N, 22.58; Cl 9.46. Found: C, 54.12; H, 5.01; N, 22.46; Cl 9.30.

EXAMPLE 3

(a) Preparation of the starting compound

A solution of 2-aminopyrimidine (1.9 g.) in dried dimethylformamide (8 ml.) was dropwise added to a suspension of 50% sodium hydride (1.25g.) in dried dimethylformamide (2 ml.) under ice-cooling, and the mixture was stirred for 15 minutes at the same temperature and for 2 hours at ambient temperature. Bromoacetaldehyde diethyl acetal (4.3 g.) and dried dimethylformamide (2 ml.) were added thereto, and the mixture was stirred for 2 hours and 20 minutes at ambient temperature and for 2.5 hours at 80° C. The reaction mixture was cooled to at ambient temperature and to the mixture was added water, and then the mixture was extracted 3 times with ethyl acetate. The extract was washed with water and a saturated sodium chloride aqueous solution in turn, and dried over magnesium sulfate. The solvent was distilled off under reduced pressure and the residual oil was purified by column chromatography on silica gel (25 g.) using chloroform as developing solvent to give 2-pyrimidinylaminoacetaldehyde diethyl acetal (1.4 g.), oil. This oil was allowed to stand to give crystals.

Infrared Absorption Spectrum (Nujol) 1616, 1580, 1542, 1066 cm$^{-1}$.

Nuclear Magnetic Resonance Spectrum (d$_6$-DMSO, δ) ppm 8.23 (2H, d, J=4.5Hz); 7.00 (1H, m); 6.56 (1H, t, J=4.5Hz); 4.60 (1H, t, J=5Hz); 3.50 (6H, m); 1.10 (6H, t, J=7Hz).

(b) Preparation of the object compound

2-Pyrimidinylaminoacetaldehyde diethyl acetal (4 g.) and 3,4-dihydroxyphenethylamine hydrochloride (2.76 g.) were dissolved in a mixture of ethanol (18 ml.) and water (5 ml.) with heating, and conc. hydrochloric acid (0.9 ml.) was dropwise added thereto, after which the mixture was refluxed for 5 hours. After the reaction, the precipitated yellow crystals were collected by filtration and washed with acetone. The crystals were recrystallized twice from water and dried under reduced pressure to give 1-(2-pyrimidinyl)-aminomethyl-6,7-dihydroxy-1,2,3,4-tetrahydroisoquinoline dihydrochloride (1.7 g.), mp 275° to 283° C (dec.).

Infrared Absorption Spectrum (Nujol) 1646, 1462 cm$^{-1}$.

Nuclear Magnetic Resonance Spectrum (d$_6$-DMSO, δ) ppm 10.0 (1H, broad s); 9.40 (1H, broad s); 8.59 (2H, d, J=5Hz); 8.26 (1H, m); 6.93 (1H, t, J=5Hz); 6.77 (1H, s); 6.58 (1H, s); 4.50 (1H, m); 3.93 (2H, m); 3.30 (2H, m); 2.86 (2H, m).

Analysis Calcd. for $C_{14}H_{18}O_2N_4Cl_2$: C, 48.71; H, 5.25; N, 16.23; Cl 20.54. Found: C, 48.34; H, 5.48; N, 16.00; Cl 19.77.

EXAMPLE 4

(a) Preparation of the starting compound

A solution of 2-bromo-1,3,4-thiadiazole (3.14 g.) and aminoacetaldehyde diethyl acetal (5.1 g.) in benzene (75 ml) was refluxed for 20 hours. After cooling, the insoluble material was filtered off. The filtrate was concentrated under reduced pressure to give oil (6.3 g.). The oil was purified by column chromatography on silica gel (120 g.) using benzene and then ethyl acetate as developing solvent to give (1,3,4-thiadiazol-2-yl)aminoacetaldehyde diethyl acetal (3.3 g.), mp 108° to 112° C.

I.R. spectrum (Nujol) 3130, 2940, 1555, 1494 cm$^{-1}$.

N.M.R. spectrum (CDCl$_3$, δ); ppm 11.7 (1H, broad s); 8.00 (1H, s); 4.77 (1H, t, J=5.8Hz); 4.17 (2H, d, J=5.8Hz); 3.70 (4H, m); 1.20 (6H, t, J=7Hz).

(b) Preparation of the object compound

Conc. hydrochloric acid (2 drops) was added to a solution of 3,4-dihydroxyphenethylamine hydrochloride (1.8 g.) and (1,3,4-thiadiazol-2-yl)aminoacetaldehyde diethyl acetal (3.1 g.) in a mixture of ethanol (60 ml) and water (15 ml.). The resulting mixture was refluxed for 18 hours. After cooling, the reaction mixture was allowed to stand at ambient temperature. Precipitating crystals were collected by filtration and washed with ethanol to give 1-(1,3,4-thiadiazol-2-yl)aminomethyl-6,7-dihydroxy-1,2,3,4-tetrahydroisoquinoline hydrochloride (1.0 g.).

I.R. spectrum (Nujol) 2900, 1622, 1605, 1562, 1530 cm$^{-1}$.

N.M.R. spectrum (d$_6$-DMSO, δ); ppm 9.20 ~ 9.80 (5H, m); 8.67 (1H, s); 6.87 (1H, s); 6.67 (1H, s); 5.00 (1H, m); 4.50 (2H, m); 3.33 (2H, m); 3.00 (2H, m).

EXAMPLE 5

(a) Preparation of the starting compound (1) A solution of 4-aminopyridine (23.2 g.) in a mixture of dried hexamethylphosphoric triamide (45 g.) and dried dimethylformamide (80 ml) was dropwise added over 20 minutes with stirring and ice-cooling to a suspension of 65.5% sodium hydride (10 g.) in dried dimethylformamide (20 ml.). After dried dimethylformamide (20 ml.) was further added thereto, the mixture was stirred for 1 hour under ice-cooling, for 20 minutes at ambient temperature and for 40 minutes at 50° C. A solution of bromoacetaldehyde diethyl acetal (54 g.) in dried dimethylformamide (20 ml.) was dropwise added thereto over 5 minutes at 50° C. The resulting mixture was stirred for 15 hours at 80° C and for 3 hours at 100° C. After cooling, water was added to the reaction mixture and the resulting mixture was concentrated under reduced pressure to remove dimethylformamide. To the residue was added water and the mixture was extracted with ethyl acetate. The extract was in turn washed 3 times with water and once with a saturated sodium chloride aqueous solution and dried over magnesium sulfate. The solvent was distilled off under reduced pressure and the residual oil was purified by column chromatography on alumina (300 g.) using a mixture of ethyl acetate and hexane (1 : 1) as a developing solvent to give oil of 4-pyridylaminoacetaldehyde diethyl acetal (7.0 g.).

I.R. spectrum (Film) 3260, 1600, 1122, 1060 cm$^{-1}$.
N.M.R. spectrum (CCl$_4$, δ)
ppm 8.08 (2H, broad d, J=5.6Hz); 6.50 (2H, broad d, J=5.6Hz); 4.58 (1H, t, J=5.6Hz); 3.55 (6H, m); 1.20 (6H, t, J=7Hz).

(2) A solution of 4-pyridylaminoacetaldehyde diethyl acetal (7.0 g.) in a mixture of dried dimethylformamide (20 ml.) and dried hexamethylphosphoric triamide (7.5 ml.) was dropwise added over 5 minutes under ice-cooling and stirring to a suspension of 65.5% sodium hydride (2.0 g.) in dried dimethylformamide (3 ml.). The mixture was stirred for 10 minutes at ambient temperature, for 30 minutes at 60° C and for 15 minutes under ice-cooling. A solution of benzyl chloroformate (9.0 g.) in dried dimethylformamide (2 ml.) was dropwise added thereto under stirring and ice-cooling. The resulting mixture was stirred for 20 minutes under ice-cooling and for 15 minutes at ambient temperature. After water was dropwise added to the reaction mixture, the mixture was extracted 3 times with ethyl acetate. The extract was in turn washed twice with water and once with a saturated sodium chloride aqueous solution and dried over magnesium sulfate. The solvent was distilled off under reduced pressure and the residual oil was purified by column chromatography on silica gel (60 g.) using a mixture of benzene and ethyl acetate (7 : 3) as developing solvent to give oil of N-benzyloxycarbonyl-N-(4-pyridyl)aminoacetaldehyde diethyl acetal (1.3 g.).

I.R. spectrum (Film) 1714, 1588, 1150, 1128, 1060 cm$^{-1}$. N.M.R. spectrum (d$_6$-DMSO, δ) ppm 8.50 (2H, broad d, J=5.4Hz); 7.37 (5H, s); 6.93 (2H, m); 5.20 (2H, s); 4.67 (1H, t, J=5.4Hz); 3.80 (2H, d, J=5.4Hz); 3.41 (4H, m); 1.00 (6H, t, J=6.5Hz).

(b) Preparation of the object compound

A solution of 3,4-dihydroxyphenethylamine hydrochloride (0.53 g.), N-benzyloxycarbonyl-N-(4-pyridyl)aminoacetaldehyde diethyl acetal (1.2 g.) and conc. hydrochloric acid (1 ml.) in water (6 ml.) was refluxed for 8 hours at 100° C. The reaction mixture was concentrated under reduced pressure and the crystalline residue was recrystallized from a mixture of methanol and ether to give 1-(4-pyridyl)aminomethyl-6,7-dihydroxy-1,2,3,4-tetrahydroisoquinoline dihydrochloride monohydrate (0.8 g.), mp 172° to 176° C (dec.).

I.R. spectrum (Nujol) 1640, 1532, 1460 cm$^{-1}$.

N.M.R. spectrum (d$_6$-DMSO, δ) ppm 8.27 (2H, broad d, J=7Hz); 7.10 (2H, broad d, J=7Hz); 6.80 (1H, s); 6.63 (1H, s); 4.63 (1H, m); 3.93 (2H, m); 3.40 (2H, m); 3.00 (2H, m).

EXAMPLE 6

(a) Preparation of the starting compound

A solution of 2-benzimidazolinone (11.0 g.) and conc. hydrochloric acid (1 drop) in phosphorus oxychloride (126 g.) was stirred for 14 hours at 110° C. After cooling, the mixture was concentrated under reduced pressure to remove excess phosphorus oxychloride. Water was added to the residue and sodium bicarbonate was added thereto to neutralize the mixture. The resulting mixture was extracted four times with ethyl acetate. The combined ethyl acetate extracts were washed with water and a saturated sodium chloride aqueous solution and dried over magnesium sulfate. The solvent was distilled off under reduced pressure to give crystals of 2-chlorobenzimidazole (11.0 g.). To the crystals were added aminoacetaldehyde diethyl acetal (35.5 g.) and dried toluene (80 ml.) and the resulting solution was stirred for 17 hours at 115° C. After cooling, the reaction mixture was extracted by adding a sodium bicarbonate aqueous solution and ethyl acetate. The aqueous layer was further extracted twice with ethyl acetate. The combined ethyl acetate layers were washed with water and a saturated sodium chloride aqueous solution and then dried over magnesium sulfate. The solvent was distilled off under reduced pressure to give oil. The oil was crystallized by adding benzene and hexane to give 2-benzimidazolylaminoacetaldehyde diethyl acetal (11.0 g.), mp 117° to 121° C. The mother liquor was purified by column chromatography on silica gel (100 g.) using a mixture of ethyl acetate and benzene (1:1) to give the same compound (1.5 g.).

I.R. spectrum (Nujol) 3360, 1648, 1608, 1588, 1054 cm$^{-1}$.

N.M.R. spectrum (d$_6$-DMSO, δ); ppm 7.00 (4H, m); 6.40 (1H, broad s); 4.67 (1H, t, J=5.8Hz); 3.50 (6H, m); 1.27 (6H, t, J=7.0Hz).

(b) Preparation of the object compound

A solution of 3,4-dihydroxyphenethylamine hydrochloride (1.37 g.), 2-benzimidazolylaminoacetaldehyde diethyl acetal (2.0 g.) and conc. hydrochloric acid (0.8 ml.) in a mixture of n-butanol (7 ml.) and water (3 ml.) was stirred for 10 hours at 110° C. The reaction mixture was allowed to stand at ambient temperature and precipitating crystals were collected by filtration and washed with a mixture of methanol and ether to give crystals (2.92 g.). The crystals were dissolved in water and the solution was neutralized by adding sodium bicarbonate and extracted 3 times with methyl ethyl ketone. The combined extracts were washed with a saturated sodium chloride aqueous solution and dried over magnesium sulfate. The solvent was distilled off to give oil, which was dissolved in methanol (10 ml.). Fumaric acid (0.7 g.) was added thereto and the mixture was stirred and allowed to stand to precipitate crystals. The crystals were collected by filtration and washed with methanol to give 1-(2-benzimidazolyl)aminomethyl-6,7-dihydroxy-1,2,3,4-tetrahydroisoquinoline fumarate (2.2 g.). This material was recrystallized from a mixture of dimethylsulfoxide and water to give pure compound (1.0 g.), mp 257° to 259° C (dec.).

I.R. spectrum (Nujol) 1680, 1348, 1282 cm$^{-1}$.

N.M.R. spectrum (d$_6$-DMSO+D$_2$O+NaOH, δ); ppm 7.16 (2H, d d, J=2, 3Hz); 6.80 (2H, d d, J=2, 3Hz); 6.44 (2H, s); 6.38 (1H, s); 6.20 (1H, s); 2.8 ∼ 4.0 (6H, m).

EXAMPLE 7

(a) Preparation of the starting compound (1) A solution of 2-aminopyridine (9.4 g.) in dried toluene (25 ml.) was dropwise added at 100° C to a suspension of 55% sodium hydride (5.04 g.) in dried toluene (10 ml.). The mixture was stirred for 2 hours at 100° C. To the solution were added bromoacetaldehyde diethyl acetal (26 g.) and dried toluene (5 ml.). The mixture was stirred for 19 hours at 115° C and cooled to ambient temperature. The reaction mixture was post-treated according to similar manners to those of the above-mentioned Examples to give oil of 2-pyridylaminoacetaldehyde diethyl acetal (8 g.).

I.R. spectrum (Film) 3400, 1600, 1570, 1120, 1060 cm$^{-1}$.

N.M.R. spectrum (CDCl$_3$, δ) ppm 8.10 (1H, broad d. J=5.0Hz); 7.40 (1H, m); 6.50 (2H, m); 4.70 (1H, broad s); 4.66 (1H, t, J=6.0Hz); 3.50 (2H, d, J= 6.0Hz); 3.60 (4H, m); 1.23 (6H, t, J=7.0Hz).

(2) A solution of 2-pyridylaminoacetaldehyde diethyl acetal (8.0 g.) in a mixture of acetic anhydride (30 ml.) and pyridine (30 ml.) was stirred for 4 hours at 80° C and allowed to stand for 12 hours at ambient temperature. The reaction mixture was post-treated according to a similar manner to that of Example 5 (a) (2) to give oil of N-acetyl-N-(2-pyridyl)aminoacetaldehyde diethyl acetal (6 g.).

I.R. spectrum (Film) 1670, 1588, 1130, 1060 cm$^{-1}$.

N.M.R. spectrum (CDCl$_3$, δ) ppm 8.46 (1H, broad d, J=5.8Hz) 7.1 ∼ 8.8 (3H, m) 3.80 (1H, t, J=5.8Hz) 3.62 (2H, d, J=5.8Hz) 3.57 (4H, m) 2.10 (3H, s) 1.13 (6H, t, J=7.0Hz).

(3) A mixture of N-acetyl-N-(2-pyridyl)-aminoacetaldehyde diethyl acetal (6.0 g.), methyl iodide (25 g.) and ethanol (30 ml.) was heated for 15 hours at 60° C in a sealed tube. The reaction mixture was concentrated and water was added to the residual oil. The mixture was washed twice with ether and the aqueous layer was concentrated under reduced pressure to give oil of 1-methyl-2-[N-acetyl-N-(2,2-diethoxyethyl)-amino]-pyridinium iodide (9.0 g.).

(b) Preparation of the object compound

A solution of 3,4-dihydroxyphenethylamine hydrochloride (2.6 g.) and 1-methyl-2-[N-acetyl-N-(2,2-diethoxyethyl)amino]-pyridinium iodide (9.0 g.) which was obtained above in a mixture of n-butanol (20 ml.) and water (3 ml.) was stirred for 7 hours at 100° C. The reaction mixture was concentrated under reduced pressure to give oil. The oil was dissolved in a mixture of water and methanol, to which was added acetone and the mixture was allowed to stand to precipitate oil. The acetone layer was separated and the oil was again dissolved in a mixture of water and methanol. To the solution was added acetone to precipitate oil. The acetone layer was separated and combined with the previously separated acetone layer. The combined acetone layers were allowed to stand to precipitate crystals. The crystals were collected by filtration, washed with acetone and dried to give 1-methyl-2-[(6,7-dihydroxy-1,2,3,4-tetrahydroisoquinolin-1-yl) methylamino] pyridinium iodide hydriodide (1.0 g.). This compound was recrystallized from a mixture of methanol and water to give pure compound (0.7 g.), mp 277° to 280° C (dec.).

I.R. spectrum (Nujol) 1640, 1588, 1532 cm$^{-1}$.

N.M.R. spectrum (d$_6$-DMSO, δ) ppm 8.9 ~ 9.30 (5H, m); 7.90 ~ 8.35 (2H, m); 6.90 ~ 7.60 (2H, m); 6.77 (1H, s); 6.60 (1H, s); 4.67 (1H, m); 3.93 (3H, s); 3.90 (2H, m); 3.33 (2H, m); 2.87 (2H, m). Analysis Calcd. for C$_{16}$H$_{21}$O$_2$N$_3$I$_2$: C, 35.51; H, 3.91; N 7.77. Found: C, 35.58; H, 3.82; N, 7.85.

What we claim is:

1. 1,2,3,4-Tetrahydroisoquinolines of the formula:

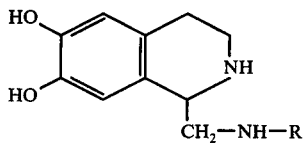

wherein R is tetrazolyl,
pyridyl,
pyrimidinyl,
thiadiazolyl or
benzimidazolyl, each of which may be substituted by C$_{1-6}$ alkyl, phenyl or alkylphenyl group having 7–10 carbon atoms; or pharmaceutically acceptable salts thereof.

2. The compounds of claim 1, wherein R is tetrazolyl which may be substituted by C$_{1-6}$ alkyl, phenyl or alkylphenyl group having 7–10 carbon atoms,
pyridyl,
pyrimidinyl,
thiadiazolyl or
benzimidazolyl.

3. The compounds of claim 2, wherein R is tetrazolyl which may be substituted by C$_{1-6}$ alkyl, phenyl or alkylphenyl group having 7–10 carbon atoms.

4. The compounds of claim 3, wherein R is tetrazolyl substituted with one C$_{1-6}$ alkyl, one phenyl or one alkylphenyl group having 7–10 carbon atoms.

5. The compounds of claim 4, wherein R is tetrazolyl substituted with one methyl or one phenyl group.

6. The compound of claim 5, which is 1-(1-methyl-1H-tetrazol-5-yl) aminomethyl-6,7-dihydroxy-1,2,3,4-tetrahydroisoquinoline hydrochloride trihemihydrate.

7. The compound of claim 5, which is 1-(1-methyl-1H-tetrazol-5-yl) aminomethyl-6,7-dihydroxy-1,2,3,4-tetrahydroisoquinoline dihydrochloride.

8. The compound of claim 5, which is 1-(1-methyl-1H-tetrazol-5-yl) aminomethyl-6,7-dihydroxy-1,2,3,4-tetrahydroisoquinoline hemifumarate.

9. The compound of claim 5, which is 1-(1-phenyl-1H-tetrazol-5-yl) aminomethyl-6,7-dihydroxy-1,2,3,4-tetrahydroisoquinoline hydrochloride.

10. The compounds of claim 2, wherein R is pyridyl.

11. The compound of claim 10, which is 1-(4-pyridyl)-aminomethyl-6,7-dihydroxy-1,2,3,4-tetrahydroisoquinoline dihydrochloride monohydrate.

12. The compound of claim 10, which is 1-methyl-2-[(6,7-dihydroxy-1,2,3,4-tetrahydroisoquinolin-1-yl)-methylamino]pyridinium iodide hydriodide.

13. The compounds of claim 2, wherein R is pyrimidinyl.

14. The compound of claim 13, which is 1-(2-pyrimidinyl)aminomethyl-6,7-dihydroxy-1,2,3,4-tetrahydroisoquinoline dihydrochloride.

15. The compounds of claim 2, wherein R is thiadiazolyl.

16. The compound of claim 15, which is 1-(1,3,4-thiadiazol-2-yl) aminomethyl-6,7-dihydroxy-1,2,3,4-tetrahydroisoquinoline hydrochloride.

17. The compounds of claim 2, wherein R is benzimidazolyl.

18. The compound of claim 17, which is 1-(2-benzimidazolyl)aminomethyl-6,7-dihydroxy-1,2,3,4-tetrahydroisoquinoline fumarate.

19. A pharmaceutical composition, comprising: an amount of a compound of claim 1 effective for relaxing smooth muscles in association with a pharmaceutically acceptable, substantially non-toxic carrier or excipient.

20. A method of achieving a relaxing effect on smooth muscles, which comprises:
administering a pharmaceutically effective amount of a compound of claim 1 to a host animal.

* * * * *